United States Patent [19]

Richter, Jr. et al.

[11] 4,354,110

[45] Oct. 12, 1982

[54] CHAMBER FOR MEASURING GAMMA RAY EMISSIONS

[75] Inventors: Albert P. Richter, Jr., Houston; Ronald L. Campsey, Alief, both of Tex.

[73] Assignee: Texaco Inc., White Plains, N.Y.

[21] Appl. No.: 172,748

[22] Filed: Jul. 28, 1980

[51] Int. Cl.³ .............................................. G01N 23/00
[52] U.S. Cl. .............................. 250/358.1; 250/359.1
[58] Field of Search ................... 250/269, 270, 358 R, 250/359, 360

[56] References Cited

U.S. PATENT DOCUMENTS 4,190,768 2/1980 Arnold et al. ...................... 250/359

4,266,132 5/1981 Marshall ............................... 250/359

Primary Examiner—Alfred E. Smith
Assistant Examiner—Janice A. Howell
Attorney, Agent, or Firm—Carl G. Ries; Robert A. Kulason; Henry C. Dearborn

[57] ABSTRACT

A chamber structure for use in making gamma ray emission measurements of a fluid that is subjected to bombardment from a neutron source. It has cross pipes for permitting insertion of measuring instruments into the chamber. And, there are liner sleeves inside the chamber and outside the cross pipes to hold in place and protect a layer of boron for reducing background noise from the iron in the chamber and the cross pipes.

4 Claims, 2 Drawing Figures

U.S. Patent  Oct. 12, 1982  4,354,110
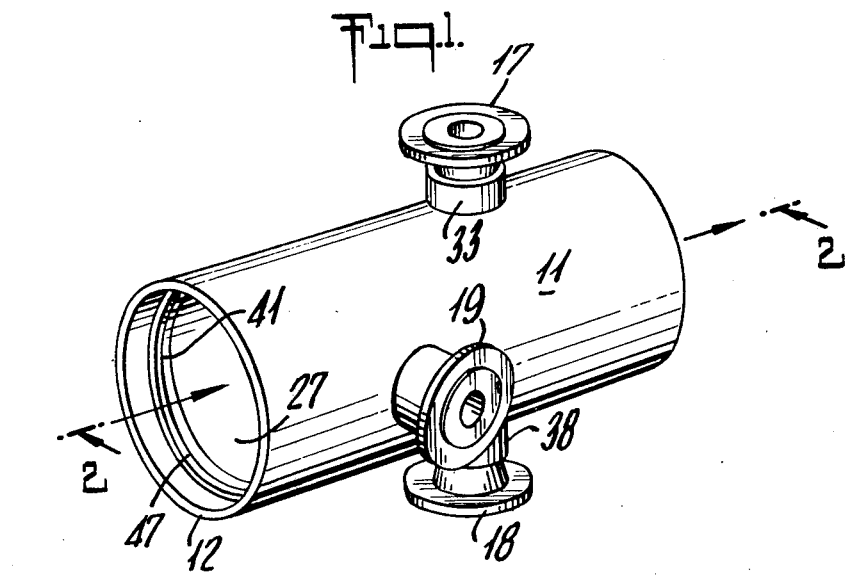
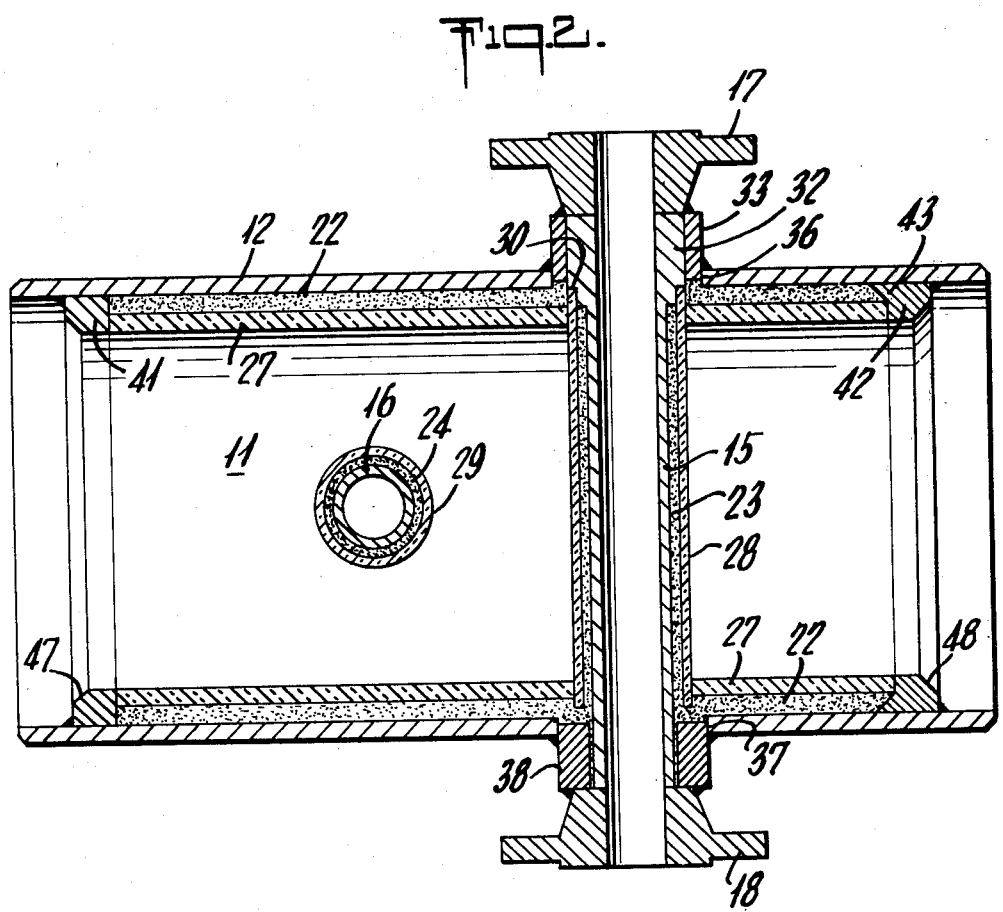

CHAMBER FOR MEASURING GAMMA RAY EMISSIONS

BACKGROUND OF THE INVENTION

1. Field of the Invention

This invention concerns the structure of a chamber that is for use in making gamma ray emission measurements of a fluid that is subjected to bombardment from a neutron source.

2. Description of the Prior Art

A recent patent, U.S. Pat. No. 4,190,768, issued Feb. 26, 1980, deals with a system for determining the water cut and water salinity in an oil-water flow stream by measuring the chlorine and the sulfur content of the produced oil. Such system includes a chamber through which the fluid stream flows. The chamber is the location for instrumentation that makes the desired determination by bombarding the fluid with neutrons, and high energy gamma rays resulting from capture of thermal neutrons are detected. Then, the spectra of the detected gamma rays are analyzed to determine the relative presence of the elements, sulfur, hydrogen and chlorine. In that system the chamber employed for mounting the instrumentation is preferably manufactured of some material which contains no elements producing appreciable capture gamma radiation above 5.0 Me V. However, as indicated if the material used is iron, it would be desirable to coat the internal surfaces of the chamber with a material of high thermal neutron cross capture cross section, e.g. by painting on a boron carbide, epoxy mixture. But, while that technique reduced the background noise there were difficulties which involved such problems as the surface of the coated area not being smooth so that the erosion of material was high. Also, the coating technique was time consuming and costly, plus the fact that problems were encountered in curing the mixture. In addition, the coating did not turn out to be uniform in thickness and so tended to result in increased background noise.

Consequently, it is an object of this invention to provide an improved chamber structure that makes a highly satisfactory protective layer of boron carbide readily applicable to the desired surfaces of a chamber to be used for the indicated gamma ray emission meaurement.

SUMMARY OF THE INVENTION

Briefly, the invention is in combination with a chamber for making measurements using irradiation with neutrons and gamma radiation emission detection. The said chamber has iron walls for containing a fluid to be measured, and the improvement comprises cross pipe means for locating a neutron source and a detector in said fluid. The improvement also comprises the said cross pipe means having iron walls, and means for covering all said iron walls with material having high thermal neutron capture cross section to reduce background noise.

Again briefly, the invention is in combination with a cylindrical chamber for permitting a flow of crude oil to make measurements of small amounts of chlorine therein by using irradiation with neutrons and detecting characteristic energy levels of gamma rays. The said chamber has iron walls, and the improvement comprises a pair of pipes having iron walls and located diametrically across said chamber for permitting insertion of instruments to make said measurements. The said pipes are spaced apart axially in said chamber to permit said crude oil to flow in between, and said pipes are constructed with a layer of boron carbide-epoxy mixture poured into a peripheral space between the outsides and the insides of epoxy-glass sleeves surrounding said pipes. Also, said chamber is constructed with a layer of boron carbide-epoxy mixture, poured into a peripheral space between the inside of said chamber walls and the outside of an epoxy-glass sleeve inside said chamber.

BRIEF DESCRIPTION OF THE DRAWINGS

The foregoing and other objects and benefits of the invention will be more fully set forth below in connection with the best mode contemplated by the inventors of carrying out the invention, and in connection with which there are illustrations provided in the drawings, wherein:

FIG. 1 is a perspective showing a chamber unit in accordance with the invention; and FIG. 2 is an enlarged longitudinal cross-section of the chamber illustrated in FIG. 1, taken along the lines 2—2 and looking in the direction of the arrows.

DESCRIPTION OF THE PREFERRED EMBODIMENT

Referring to the drawings, it will be noted that there is a cylindrical chamber 11 that has open ends which are adaptable for being connected to permit a flow of the material to be measured, e.g. crude oil to flow therethrough. The chamber 11 has iron walls 12, and there are a pair of cross pipes 15 and 16 which also have iron walls. These pipes 15 and 16 are open at the ends for inserting instruments (not shown) to make the desired measurements. They may have flanges as illustrated, for mounting flange valves (not shown) in case a leak should develop. Thus, there are flanges 17 and 18 on the ends of pipe 15. They are welded in place, as indicated. Similarly, there are a pair of flanges on the ends of the pipe 16. Thus, there is a flange 19 on the end of the pipe 16 which shows in FIG. 1.

The construction for reducing background noise from the iron of the chamber and the pipe walls, includes the use of a layer of boron carbide-epoxy mixture. Such a layer 22 is on the inside of the iron walls 12 of the chamber 11. Similarly, there are layers 23 and 24 of the same material (a boron carbide-epoxy mixture) that surrounds the iron pipes 15 and 16 respectively. As will be explained in more detail hereafter, such layers of the boron carbide-epoxy mixture are poured into place inside of the spaces formed between the wall 12 and an inner sleeve 27 of the chamber 11, as well as into the spaces between the iron pipes 15 and 16 and a pair of sleeves 28 and 29 respectively, that surround the pipes 15 and 16.

It may be noted that the construction of the cross pipes 15 and 16 includes the dimensions of wall thickness, as indicated. These may be produced by machining the pipes to provide shoulders e.g. a shoulder 30 on the pipe 15, which are for fitting the sleeves 28 and 29 onto the pipes 15 and 16 with the outside diameters flush with the diameters of the pipe ends. Thus, there is an end 32 on the pipe 15 which end is surrounded by a short nipple 33. Nipple 33 is welded into place in a hole 36 that is cut through the wall 12 of the chamber 11.

At the other end of the pipe 15 there is another hole 37 cut through the wall 12 of the chamber 11. Into the hole 37 there is fitted another nipple 38 to which the flange 18 is welded in like manner as the nipple 33 and the flange 17.

The construction of the chamber 11 includes a pair of transition rings 41 and 42 on the inside near the ends. These are welded into place as the construction is finalized. However, it may be noted that the ring 42 would be first. Thereafter, the sleeve 27 would be inserted and automatically centered as it contacts the ring 42 by a shoulder 43 that faces inward toward the center of the chamber 11. This shoulder 43 has an angle of approximately 45° so that the sleeve 27 will contact it when the sleeve is inserted into the chamber 11 prior to mounting the other ring 41. In this manner, when the end of the sleeve 27 reaches the ring 42, it will be centered coaxially with the walls 12 of the chamber 11. Then, as will appear more fully below, the other end of the sleeve 27 may be wedged to center it before the layer 22 is applied and the ring 41 is welded in place.

It may be noted that the nipples 33 and 38 are employed in order to prevent excess heat from damaging the exoxy. Consequently, the nipples 33 and 38 (as well as the two not shown for the other cross pipe 16) are welded in place in the holes 36 and 37. The latter are machined in the walls 12 of the chamber 11. Thereafter, the nipples (e.g. nipples 33 and 38) will allow welding of the ends of the cross pipes 15 and 16 where the flanges (e.g. flanges 17, 18 and 19) are welded on, to dissipate the heat without damage to the epoxy.

In constructing the cross pipes 15 and 16, it may be noted that they are first machined to the proper dimensions, as indicated above, so that the sleeves 28 and 29 may be fitted onto the shoulder at one end, e.g. the shoulder 30 at the end 32 of the pipe 15. Then, the layers 23 and 24 of boron carbide-epoxy mixture may be poured into the space between the sleeves 28 and 29 with the one end of each in place, as indicated. Next, one flange, e.g. the flange 17 is welded in place onto the end 32 of the pipe 15. Then the cross pipes are ready for being installed and welded in place.

As already indicated, prior to installing the cross pipes 15 and 16, one of the transition rings, i.e. the ring 42 is welded in place within the walls 12 of the chamber 11. Then, following the application of a silicone rubber sealing compound (not shown) around the ring 42 in order to seal the sleeve 27, the latter is mounted and centralized within the chamber 11. Next, the holes necessary in the sleeve 27 will be cut with a hole saw, and the cross pipes 15 and 16 are then installed and welded in place. Thereafter, the other flange in each case, e.g. flange 18, is welded onto the outer end of the other nipple, e.g. nipple 38 of the pipe 15.

A next step in constructing the chamber is to place it in a vertical position with the ring 42 at the bottom, and then heating the structure in an oven capable of bringing the assembly temperature to 80° C. The epoxy-boron carbide mixture is also heated to 80° C. with catalyst and immediately poured into the cavity or space where the layer 22 will be formed. With such procedure the boron carbide-epoxy mixture has a viscosity approximating 10W oil which flows freely into the space with a minimum of air entrapment. Preferably the epoxy-boron carbide mixture is eighty parts of 320 mesh boron carbide to one hundred parts epoxy by weight. The unit is then allowed to cure at 80° C. for eight hours and then cooled gradually overnight. A bead of silicone rubber sealing compound will be placed around the top of the sleeve 27 and the other ring 41 will be welded in place.

The rings 41 and 42 have tapered surfaces 47 and 48 to allow smooth flow of the crude oil through the chamber 11.

It may be noted that the use of the epoxy-glass sleeves 27, 28 and 29 provide a space between each and the iron walls of the chamber and cross pipes respectively, which spaces contain the desired boron carbide-epoxy mixture. These epoxy-glass liners or sleeves 26, 28 and 29 are in contact with the crude oil flowing through the chamber 11 and they provide a smooth surface to minimize erosion and possible loss of the boron carbide shielding. Thus, a highly improved chamber structure is obtained for making desired measurements of the constituents of crude oil, e.g. the presence of salt content therein.

It may be noted that the purpose of the flanges on the ends of the cross pipes 15 and 16 is to provide for the possibility of a leak. In such an eventuality, the instruments may be removed and a flange valve installed to control the leak until the chamber 11 is removed from the line (not shown).

While a particular embodiment of the invention has been described above in considerable detail in accordance with the applicable statutes, this is not to be taken as in any way limiting the invention, but merely as being descriptive thereof.

We claim:

1. In combination with a chamber for making measurements using irradiation with neutrons and gamma radiation emissions detection, said chamber having iron walls for containing a fluid to be measured, the improvement comprising cross pipe means comprising a pair of diametrically extending pipes for locating a neutron source and a detector in said fluid, said pipes being perpendicular to one another and spaced apart to permit said fluid to be measured to flow in between, said cross pipe means having iron walls, and means for covering all said iron walls with a layer of boron carbide-epoxy mixture covered by epoxy-glass.

2. The invention according to claim 1, wherein said epoxy-glass layer comprises a sleeve inside said chamber and a sleeve outside of each of said cross pipes, said boron carbide-epoxy mixture filling the spaces between said chamber walls and inside sleeve and between said cross pipe walls and outside sleeves.

3. The invention according to claim 2, wherein said chamber is cylindrical for permitting said fluid to flow therethrough.

4. The combination with a cylindrical chamber for permitting a flow of crude oil to make measurements of small amounts of chlorine therein by using irradiation with neutrons and detecting characteristic energy levels of gamma rays, said chamber having iron walls, the improvement comprising a pair of pipes having iron walls and located diametrically across said chamber for permitting insertion of instruments to make said measurements, said pipes being spaced apart axially in said chamber to permit said crude oil to flow in between, said pipes being constructed with a layer of boron carbide-epoxy mixture poured into a peripheral space between the outsides and the insides of epoxy-glass sleeves surrounding said pipes, and said chamber being constructed with a layer of boron carbide-mixture poured into a peripheral space between the inside of said chamber walls and the outside of an epoxy-glass sleeve inside said chamber.

* * * * *